United States Patent
Fumuro et al.

(10) Patent No.: US 8,109,881 B2
(45) Date of Patent: *Feb. 7, 2012

(54) SPHYGMOMANOMETER

(75) Inventors: Shinichi Fumuro, Hikone (JP); Takeshi Kojima, Hikone (JP); Tsuyoshi Yuasa, Hikone (JP); Yoshitoshi Kanetsuna, Hikone (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1089 days.

This patent is subject to a terminal disclaimer.

(21) Appl. No.: 12/000,478

(22) Filed: Dec. 13, 2007

(65) Prior Publication Data
US 2008/0146950 A1 Jun. 19, 2008

(30) Foreign Application Priority Data
Dec. 14, 2006 (JP) ................................. 2006-337375

(51) Int. Cl.
*A61B 5/02* (2006.01)
(52) U.S. Cl. ...................................... 600/499; 600/490
(58) Field of Classification Search .................. 600/490, 600/499
See application file for complete search history.

(56) References Cited

U.S. PATENT DOCUMENTS

| 3,935,984 | A  | * | 2/1976  | Lichowsky et al. | 600/499 |
| 2002/0120199 | A1 | * | 8/2002  | Ogura et al. | 600/485 |
| 2005/0187485 | A1 | * | 8/2005  | Fumuro et al. | 600/499 |
| 2005/0192501 | A1 | * | 9/2005  | Sano et al. | 600/499 |
| 2005/0283085 | A1 | * | 12/2005 | Inoue et al. | 600/499 |

FOREIGN PATENT DOCUMENTS

| EP | 1 568 313 | 8/2005 |
| EP | 1 568 315 | 8/2005 |
| JP | S56-18839 | 2/1981 |
| JP | S57-180939 | 11/1982 |
| JP | H1-254145 | 10/1989 |
| JP | H4-217829 | 8/1992 |
| JP | 2000-166883 | 6/2000 |
| JP | 2004-254882 | 9/2004 |
| JP | 2005-237802 | 9/2005 |

OTHER PUBLICATIONS

Office Action issued in JP Patent Application No. 2006-337375, dated May 31, 2011, 4 pages.

* cited by examiner

*Primary Examiner* — Miranda Le
*Assistant Examiner* — Meredith Weare
(74) *Attorney, Agent, or Firm* — Bacon & Thomas, PLLC

(57) ABSTRACT

A sphygmomanometer includes a base block and a cuff block having a cuff for restricting flow of blood, the cuff block being connected to the base block in such a manner that an angle of the cuff block with respect to a horizontal plane is variable within an angular range. The sphygmomanometer further includes a spring biasing unit for returning the cuff block to a position at a predetermined angle within the variable angular range of the cuff block when the cuff block is not used.

7 Claims, 7 Drawing Sheets

SPHYGMOMANOMETER

FIELD OF THE INVENTION

The present invention relates to a sphygmomanometer to measure a blood pressure in an upper arm of a user.

BACKGROUND OF THE INVENTION

Conventionally, in a type of a sphygmomanometer capable of automatically wrapping an upper arm of a user by a cuff for restricting flow of blood, the sphygmomanometer includes a cuff block having an insertion hole through which a user can insert his/her upper arm. The cuff block has the cuff for restricting flow of blood and a wearing cuff mechanism for allowing the cuff to wrap around the upper arm by tightening the cuff. However, in a case where the insertion hole of the cuff block is fixed at a specific inclined angle, a user may not measure his/her blood pressure in an appropriate posture depending on a height of a table on which the sphygmomanometer is put and a physical size of the user.

Therefore, there is provided a sphygmomanometer in which the cuff block is pivotably connected to a base block placed on, e.g., a table, so that an inclined angle of the cuff block with respect to a horizontal plane can be changed. However, a sphygmomanometer disclosed in Japanese Patent Laid-open Application No. 2004-254882 requires a user to adjust the cuff block and keep the angle of the cuff block by using the other arm.

SUMMARY OF THE INVENTION

The present invention provides a sphygmomanometer capable of allowing a user to easily measure a blood pressure at a proper posture.

In accordance with an aspect of the present invention, there is provided a sphygmomanometer including a base block; a cuff block having a cuff for restricting flow of blood, the cuff block being connected to the base block in such a manner that an angle of the cuff block with respect to a horizontal plane is variable within an angular range; and a spring biasing unit for returning the cuff block to a position at a predetermined angle within the variable angular range of the cuff block when the cuff block is not used.

With such arrangements, the cuff block is kept always in a state that a user can easily insert his/her arm into the cuff block. Further, while the user inserts the arm into the cuff block, the inclined angle of the cuff block is changed depending on the angle of the arm. Therefore, the blood pressure can be easily measured in a comfortable posture.

Preferably, the predetermined angle is an angle frequently used in the blood pressure measurement.

Further, if the predetermined angle is freely adjustable, a more reliable measurement can be obtained.

The sphygmomanometer may further include a lock unit to restrict the change in the angle of the cuff block with respect to the base block so that it is convenient to keep and carry the sphygmomanometer.

The sphygmomanometer may further include an elbow supporting block provided with an elbow support for supporting an elbow of a user who inserts his/her arm into the cuff block on the top surface thereof. The elbow supporting block is slidably supported on the base block and is connected to the cuff block, so that the elbow supporting unit slides on the base block in accordance with the angular change of the cuff block with respect to the base block. Accordingly a distance from one end of the cuff block to the elbow support is maintained constant even when the angle of the cuff block is changed with respect to the base block. Therefore, a precise blood pressure measurement can be carried out.

Further, the cuff block may be connected to the base block in such a manner that its horizontal position and its orientation about a vertical axis thereof are variable with respect to the base block or its vertical position is variable with respect to the base block. Therefore, a degree of freedom of the user's arm increases, so that the blood pressure measurement can be carried out at a more comfortable posture.

The sphygmomanometer may further include a detecting unit for detecting a position of the arm to the cuff block. Accordingly, the blood pressure can be measured in a state of positioning the cuff block at a proper portion of the upper arm.

In accordance with the sphygmomanometer of the present invention, the cuff block is always maintained in a state that a user can easily insert into the cuff block so that it is not necessary to apply a preliminarily manipulation of the cuff block. Further, since the inclined angle of the cuff block is changed in accordance with an angle of the arm while the arm is inserted into the cuff block, the blood pressure can be easily measured in a comfortable posture.

BRIEF DESCRIPTION OF THE DRAWINGS

The objects and features of the present invention will become apparent from the following description of preferred embodiments given in conjunction with the accompanying drawings, in which:

FIGS. 6A and 6B show a sphygmomanometer in accordance with still another embodiment of the present invention, wherein FIG. 6A is a schematic plan view depicting an operation of the sphygmomanometer and FIG. 6B shows a partial sectional view of the sphygmomanometer.

DETAILED DESCRIPTION OF THE EMBODIMENTS

Figure 1:
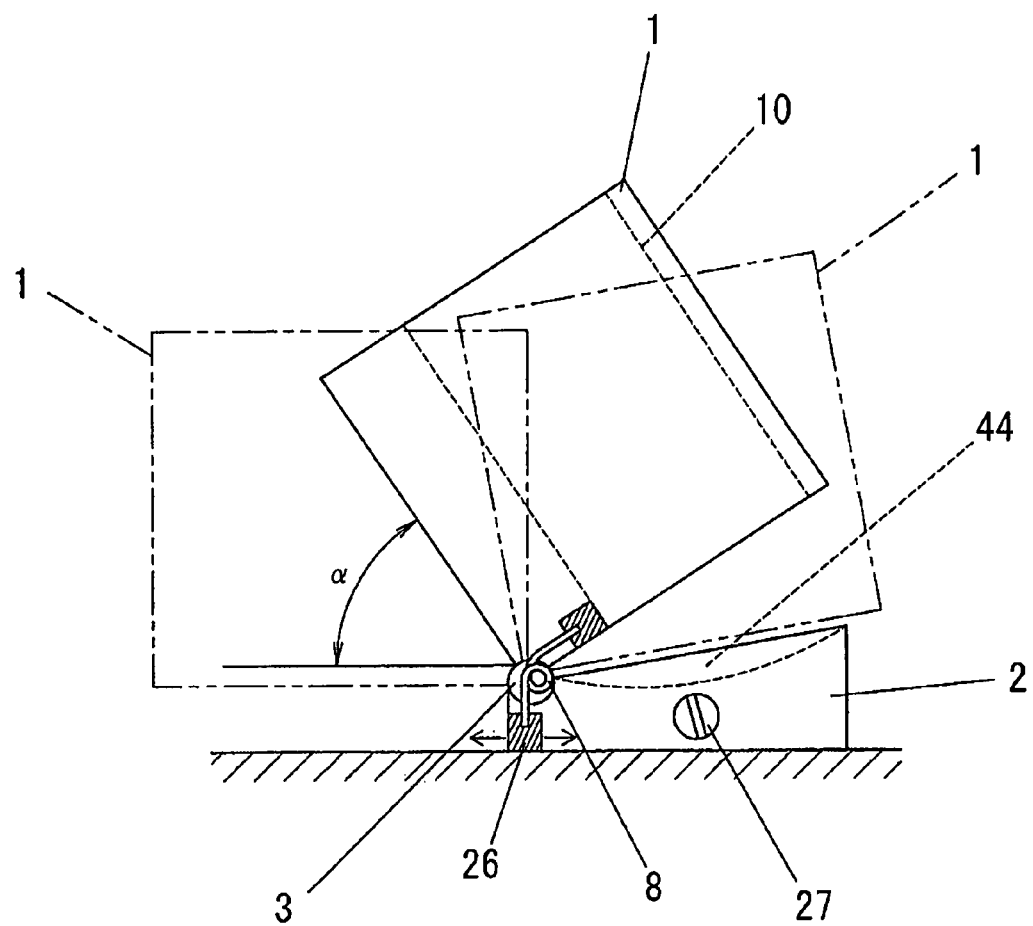
FIG. 1 shows a schematic sectional view of a sphygmomanometer in accordance with an embodiment of the present invention.

Hereinafter, embodiments of the present invention will be described in detail with reference to the accompanying drawings. Referring to FIG. 1, a cuff block 1 includes a cuff and a wearing cuff mechanism for allowing the cuff to wrap around an upper arm of a user. The cuff block has a cylindrical shape, wherein an insertion hole 10 penetrating through the cuff block is provided for inserting an upper arm. The cuff block 1 is pivotably connected through a shaft 3 to a base block 2 placed on, e.g., a table, so that an inclined angle thereof with respect to a horizontal plane is changeable. Moreover, in the vicinity of the shaft 3, a torsion spring 8 is disposed such that one end thereof is fixed to the cuff block 1 and the other end is fixed to the base block 2.

The torsion spring 8 changes the direction of its biasing force depending on the inclined angle of the cuff block 1, and maintains the cuff block 1 at a predetermined angle α with respect to the horizontal plane against the cuff block 1 falling down by its weight. Even when the cuff block 1 is pivotally moved such that the angle thereof becomes less or greater than the angle α, if releasing a force applied to the cuff block 1, the cuff block 1 is automatically returned to the position at the angle α by the biasing force of the spring 8.

Here, the predetermined angle α is preferably in a range from about 30° to 45°, but is not limited thereto. Moreover, the inclined angle of the cuff block 1 is preferably changed within a range for completely covering the range of the angle α, for example, a range between 0° to 90°.

In this case, since the cuff block 1 is normally kept inclined at the angle α, it is not necessary to change the angle in advance when a user inserts his/her arm into the cuff block 1. It is sufficient for the user to insert the arm into the insertion hole 10 of the cuff block 1. Further, while the arm is inserted through the insertion hole 10, the inclined angle of the cuff block 1 is varied depending on an angle of the arm, so that the angle of the cuff block 1 is finally identical to an angle between the upper arm inserted through the insertion hole 10 and the horizontal plane.

Further, after completing the measurement of blood pressure, the inclined angle of the cuff block 1 is varied depending on the angle of the arm while the user pulls the arm out of the cuff block 1, so that the user can smoothly pull out the arm without being hindered by the cuff block 1. Furthermore, after pulling out the arm, the cuff block 1 return to the position inclined at the angle α.

Further, when inserting the arm through the cuff block 1, a user may pivotally move the cuff block 1 toward him/her to be oriented approximately horizontal and then insert his/her arm into the cuff block 1. In this case, the cuff block 1 is pivotally moved up in accordance with an angle of the arm while the arm portion upper than the elbow is inserted through the insertion hole 10. Therefore, it is still not necessary to manually adjust the inclined angle of the cuff block 1 during the insertion of the upper arm.

Since the predetermined angle α may not be proper depending on a height of a table on which the base block 1 is placed or a physical size of a user, it is preferred to provide an adjusting dial 27 to change a spring force of the torsion spring 8 with respect to the cuff block 1 by shifting a fixing unit 26 in the base block 2 in the right-left direction in FIG. 1, the fixing unit 26 being connected to one end of the torsion spring 8. The predetermined angle α can be adjusted by shifting the fixing unit 26 with the adjusting dial 27.

Figure 2:
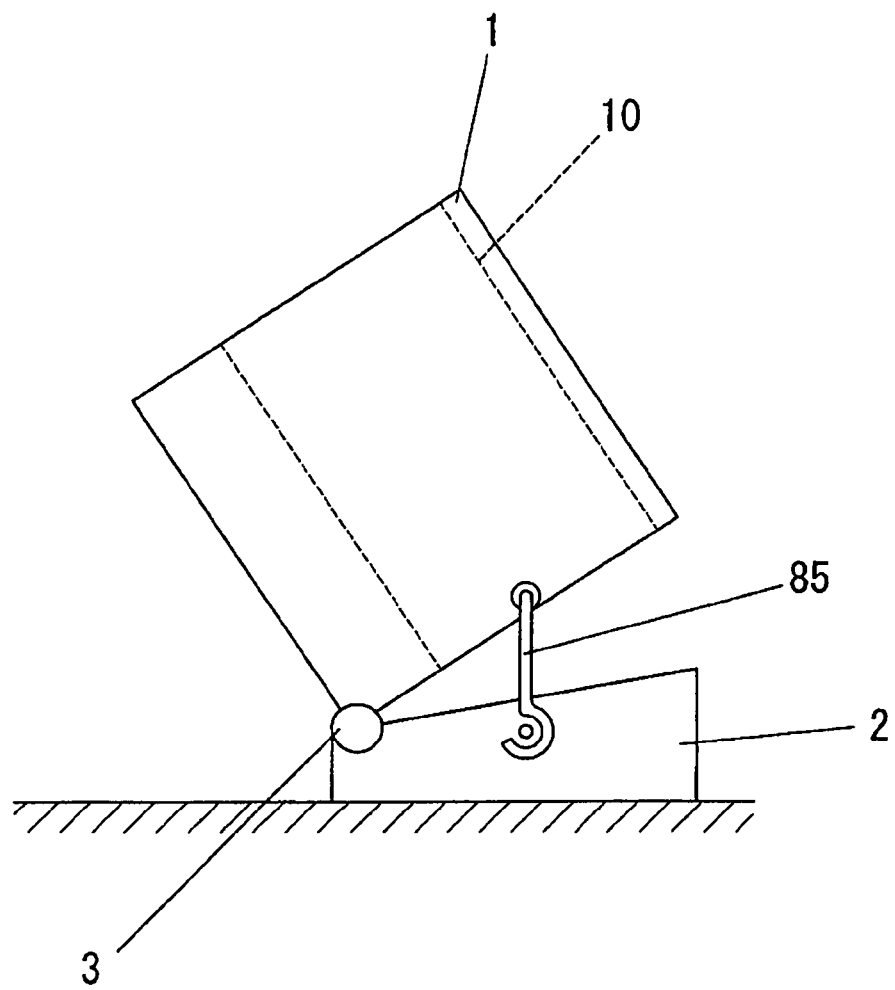
FIG. 2 shows a schematic sectional view of a modification of the sphygmomanometer.

Further, since it is preferable that the cuff block 1 is locked not to be pivotally moved with respect to the base block 2 while being carried or kept, it is preferred to provide a lock unit 85 for locking the cuff block 1 to the base block 1 as shown in FIG. 2.

Figure 3A:
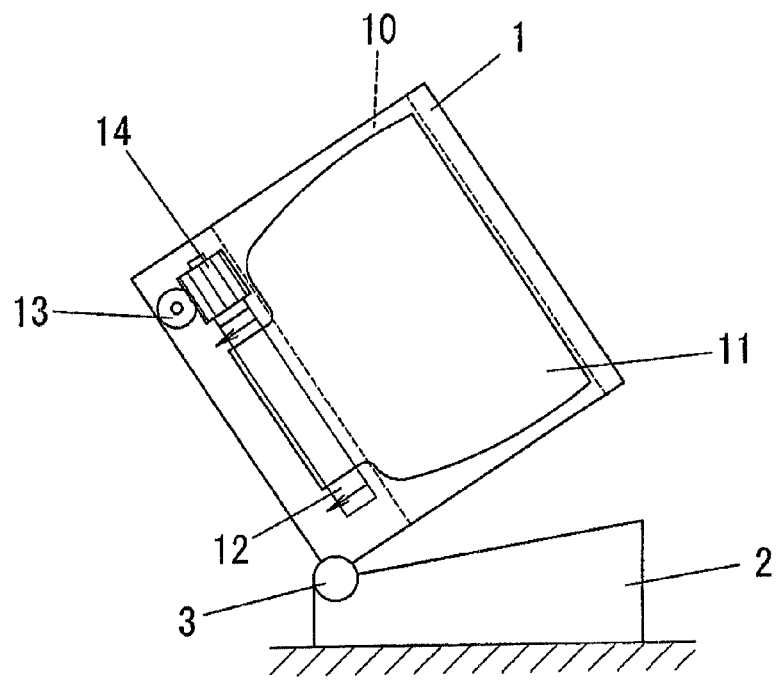
FIGS. 3A and 3B are schematic views showing a configuration in a cuff block of the sphygmomanometer.
Figure 3B:
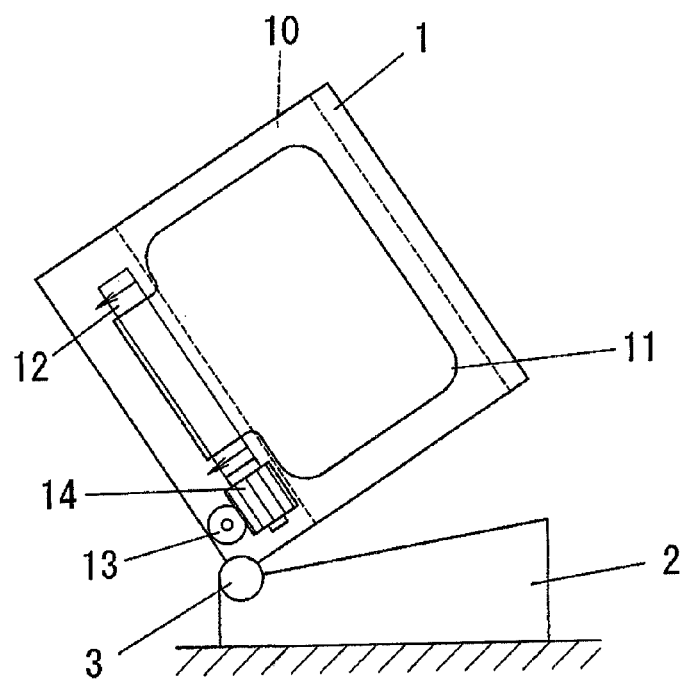

FIGS. 3A and 3B show the wearing cuff mechanism in the cuff block 1. In the drawings, reference numerals 11, 12, 13 and 14 respectively indicate the cuff, a wrap drum, a geared motor and a series of reduction gears. The wrap drum 12 is rotated by the geared motor 13 through the reduction gears 14, so that the cuff 11 is tightened or released.

Further, when the geared motor 13 and the reduction gears 14, as shown in FIG. 3A, are disposed at the opposite end portion to the end where the shaft is provided, it is easy to arrange lines or wires passing around the shaft 3 and to make the area around the shaft 3 of the base block 2 compact. Meanwhile, as shown in FIG. 3B, when the heavy geared motor 13 and reduction gears 14 are disposed around the shaft 3, a torque required to pivotally move the cuff block 1 is relatively small, so that a torsion spring 8 can be smaller.

Figure 4:
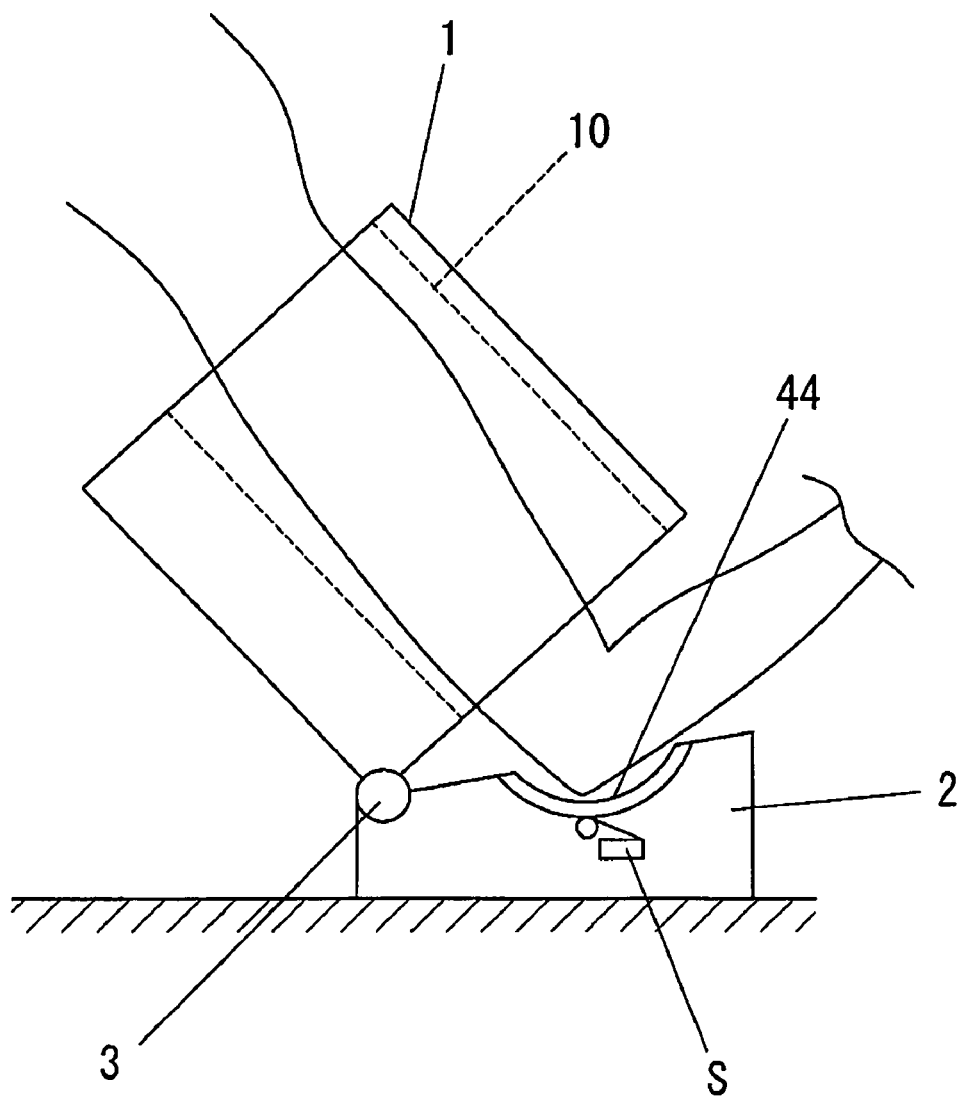
FIG. 4 shows a schematic sectional view of another modification of the sphygmomanometer.

Further, an elbow support 44 is provided on the top surface of the base block 2 to support an elbow of an arm inserted through the cuff block 1. A position of the cuff block 1 on the upper arm is determined by positioning the elbow on the elbow support 44. The elbow support 44, as shown in FIG. 4, may include a switch S to detect whether the elbow is positioned or not. In this case, an alarm sound or an alarm sign may be generated when the switch S is not turned on at the start of the blood pressure measurement, or the blood pressure measurement may be started by turning on the switch S. Therefore, it is possible to prevent the blood pressure measurement from being performed in a state where the upper arm is not sufficiently inserted into the cuff block 1.

Figure 5A:
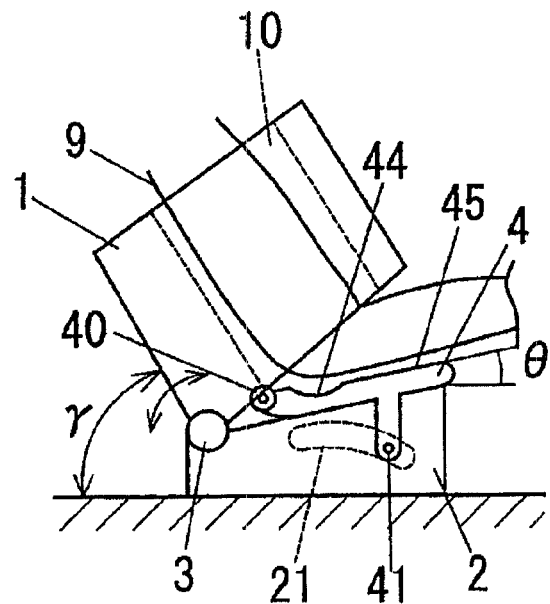
FIGS. 5A and 5B show schematic views of a sphygmomanometer in accordance with another embodiment of the present invention.
Figure 5B:
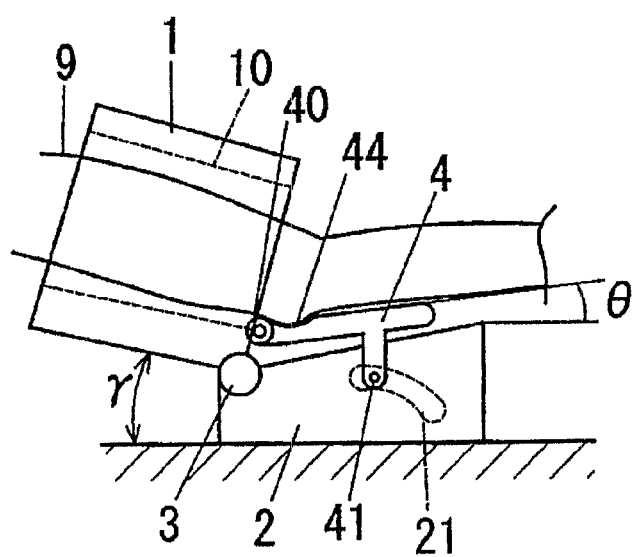
Figure 6A:
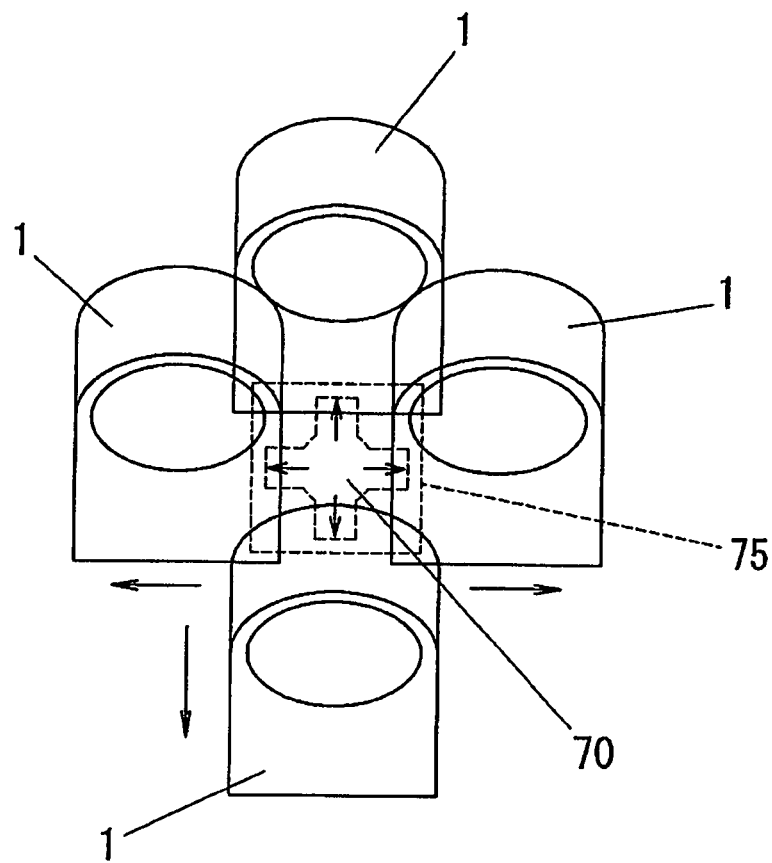
Figure 6B:
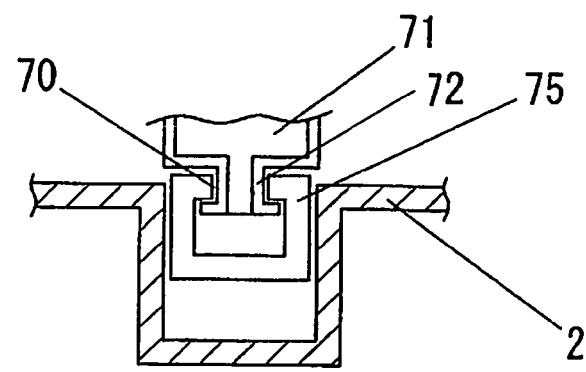
Figure 7A:
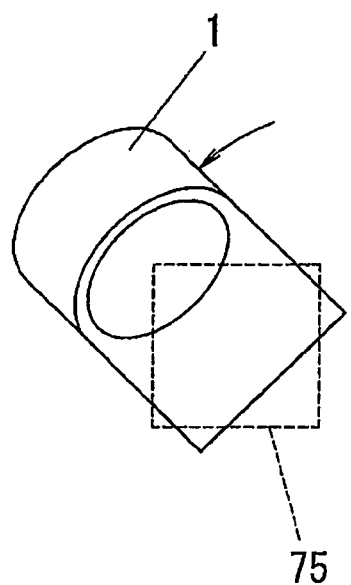
FIGS. 7A and 7B show schematic views of another operation of the sphygmomanometer.
Figure 7B:
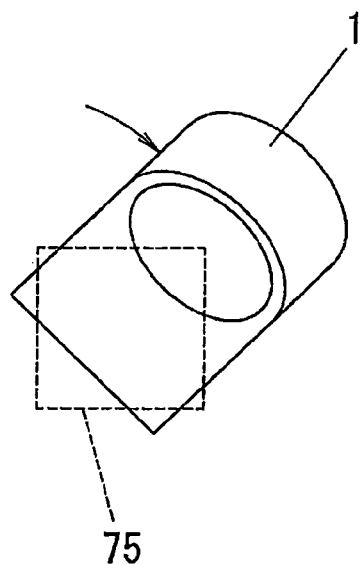

FIG. 5 shows an example for a case where the cuff block 1 is pivotably connected to the base block 2 and a member for positioning the elbow is provided on the base block 2. An elbow supporting block 4 includes an elbow support 44 for positioning an elbow of a user, and a forearm support 45 for supporting a forearm of a user. The elbow supporting block 4 is connected to the cuff block through a hinge shaft 40 at a position slightly offset from the shaft 3. Accordingly, when the cuff block 1 is pivotally moved with respect to the base block 2, the elbow supporting block 4 moves back and forward on the base block 2 in accordance with to the pivotal movement of the cuff block 1.

When a user, who inserts his/her upper arm 9 into the insertion hole 10 of the cuff block 1 for measuring his/her blood pressure, is relatively tall (or a height of a table on which the base block 2 is placed is relatively low), i.e., in case an angle γ between the cuff block 1 and the horizontal plane (an inclined angle of the cuff block 1) is comparatively large, the elbow supporting block 4 is positioned away from the shaft 3. On the contrary, when a user is relatively short (or a height of a table on which the base block 2 is placed is relatively high), i.e., in case the angle γ between the cuff block 1 and the horizontal plane (the inclined angle of the cuff block 1) is comparatively small, the elbow supporting block 4 is positioned close to the shaft 3. Accordingly, a distance from the cuff of the cuff block 1 to the elbow support 44 of the elbow supporting block 4 on which a user positions his/her elbow is kept substantially constant regardless of the inclined angle of the cuff block 1. Therefore, an accurate blood pressure measurement can be performed at any time.

The elbow supporting block 4 further includes a guide shaft 41 to slide along a guide groove 21 formed in the base block 2. Further, the guide groove 21 provided in the base block 2 has an arc shape and one end thereof away from the shaft 3 is positioned at a lower position than the other end close to the shaft 3. (The guide groove 21 may have an inclined linear shape). This is for allowing the elbow supporting block 4 to move forward and backward in accordance with the pivotal movement of the cuff block 1 while the inclined angle θ of the elbow supporting block 4 is kept unchanged. In a case where the angle θ is changed, the guide groove 21 may be a horizontal groove.

FIGS. 6A and 6B, and 7A and 7B show a sphygmomanometer in accordance with another embodiment of the present invention. In this embodiment, the cuff block 1 can change its horizontal position and its orientation about a vertical axis thereof with respect to the base block 2, and the base block 2 including a cross-shaped groove 70 formed in the top surface thereof. A movable base 71 having a bearing for the shaft 3 is provided and a shaft unit 72 of the movable base 71 is positioned in the groove 70. The shaft unit 72 has a substantially same outer diameter as a width of the groove 70. The shaft unit 72 moves along the cross-shaped groove 70 so that the position of the cuff block 1 can be shifted forward, backward, left, and right horizontally. By rotating the shaft unit 72 of the movable base 71 about its axis, the orientation of the cuff block about the vertical axis can be changed, as shown in FIG. 7.

Accordingly, even when a shoulder of a user is not aligned with the base block 2, the position and orientation of the cuff block 1 can be changed depending on the position and orientation of the user's arm. Therefore, the blood pressure measurement can be carried out in a state that the arm is maintained comfortable.

Further, in case the cross-shaped groove 70 is not directly formed in the base block 2, but is formed in a shift base 75 provided such that a vertical position thereof can be varied with respect to the base block 2, the cuff block 1 can be also shifted in the vertical position. Therefore, the blood pressure measurement can be carried out in a state that a user keeps the arm comfortable.

Further, after starting the blood pressure measurement, the measurement result is not reliable if the cuff block moves. Therefore, it is preferably to provide at least a lock unit (not shown) for preventing the movement of the movable base 71. Moreover, the change in horizontal position and orientation of the cuff block 1 is effective in view of allowing a user to keep his/her posture comfortable during the measurement even in a case where the cuff block 1 is not pivotable about the shaft 3.

While the invention has been shown and described with respect to the preferred embodiments, it will be understood by those skilled in the art that various changes and modifications may be made without departing from the scope of the invention as defined in the following claims.

What is claimed is:

1. A sphygmomanometer comprising:
   a base block;
   a cuff block having a cuff for restricting flow of blood, the cuff block being connected to the base block in such a manner that an angle of the cuff block with respect to a horizontal plane is variable within an angular range;
   a spring biasing unit for returning the cuff block to a position at a predetermined angle within the variable angular range of the cuff block when the cuff block is not used; and
   an elbow supporting block provided with an elbow support for supporting an elbow of a user who inserts his/her arm into the cuff block on the upper surface thereof, wherein the elbow supporting block is slidably supported on the base block and is connected to the cuff block, so that the elbow supporting unit slides on the base block in accordance with the angular change of the cuff block with respect to the base block.

2. The sphygmomanometer of claim 1, wherein the predetermined angle is an angle frequently used in a blood pressure measuring.

3. The sphygmomanometer of claim 1, wherein the predetermined angle is adjustable.

4. The sphygmomanometer of claim 1, further comprising a lock unit to restrict the change in the angle of the cuff block with respect to the base block.

5. The sphygmomanometer of claim 1, wherein the cuff block is connected to the base block in such a manner that its horizontal position and its orientation about a vertical axis thereof are variable with respect to the base block.

6. The sphygmomanometer of claim 1, wherein the cuff block is connected to the base block in such a manner that its vertical position is variable with respect to the base block.

7. The sphygmomanometer of claim 1, further comprising a detecting unit for detecting whether an arm of a user is properly positioned.

* * * * *